United States Patent [19]

Ash et al.

[11] 4,402,694
[45] Sep. 6, 1983

[54] BODY CAVITY ACCESS DEVICE CONTAINING A HORMONE SOURCE

[75] Inventors: Stephen R. Ash, Lafayette, Ind.; Marvin P. Loeb, Chicago, Ill.

[73] Assignee: Biotek, Inc., Arlington Heights, Ill.

[21] Appl. No.: 284,076

[22] Filed: Jul. 16, 1981

[51] Int. Cl.³ .............................................. A61M 7/00
[52] U.S. Cl. ......................................... 604/891; 3/1
[58] Field of Search ................... 128/260, 268, 213 R; 3/1; 424/19–22, 81; 521/61; 604/890, 891

[56] References Cited

U.S. PATENT DOCUMENTS 3,093,831 6/1963 Jordan ................................ 128/268
4,298,002 11/1981 Ronel et al. ........................... 424/81

FOREIGN PATENT DOCUMENTS 10865 5/1980 European Pat. Off. .................... 3/1

Primary Examiner—Richard J. Apley
Assistant Examiner—T. J. Wallen

[57] ABSTRACT

A body cavity access device for supplying a hormone to a patient including an implantable housing placed in the body and having an impermeable extracorporeal segment and a semipermeable subcutaneous segment. A hormone source such as live, hormone-producing cells, e.g., pancreatic islet cells is then removably positioned in the housing to provide a hormone supply to the patient. A sensor can be located within the subcutaneous segment and operably associated with a dispenser to release medication into the housing and to the patient.

20 Claims, 7 Drawing Figures

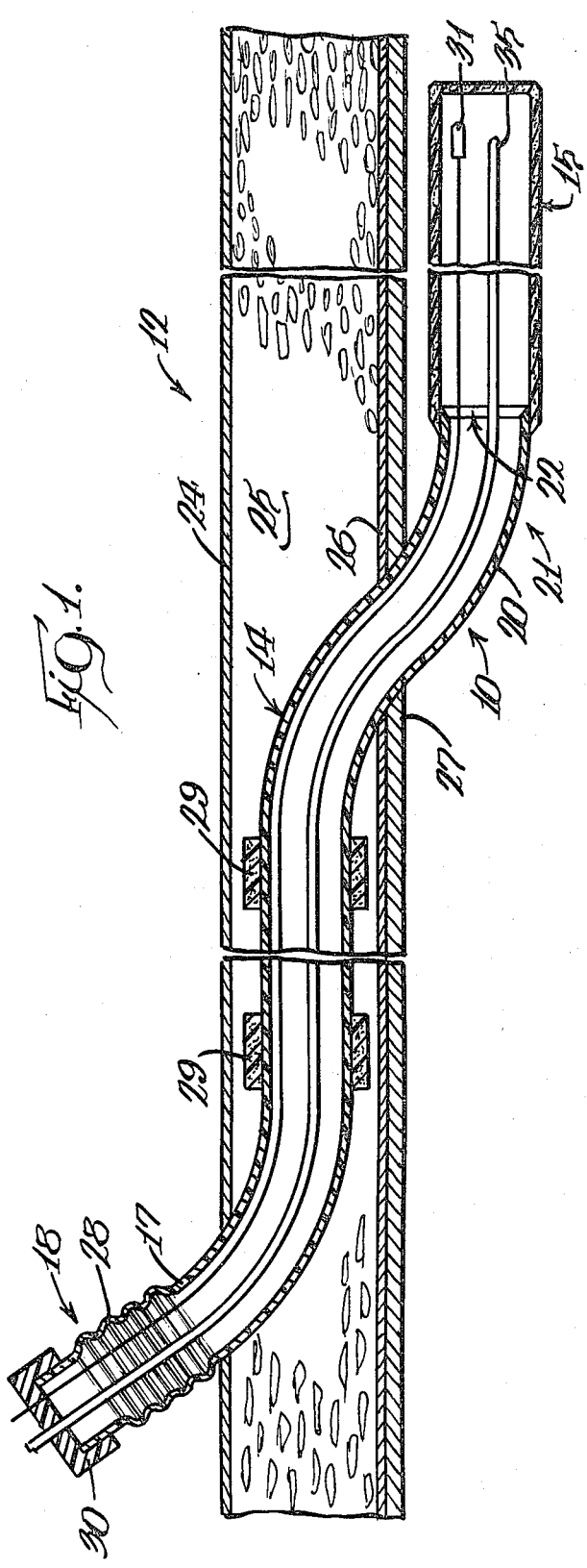
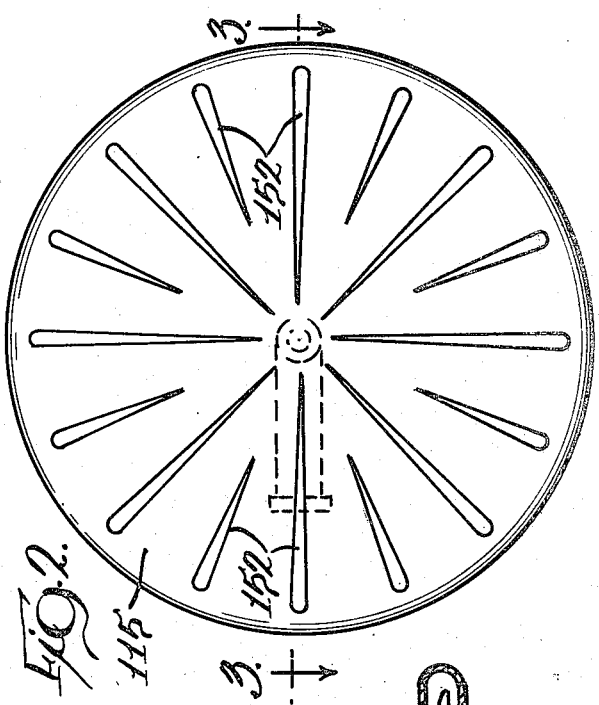
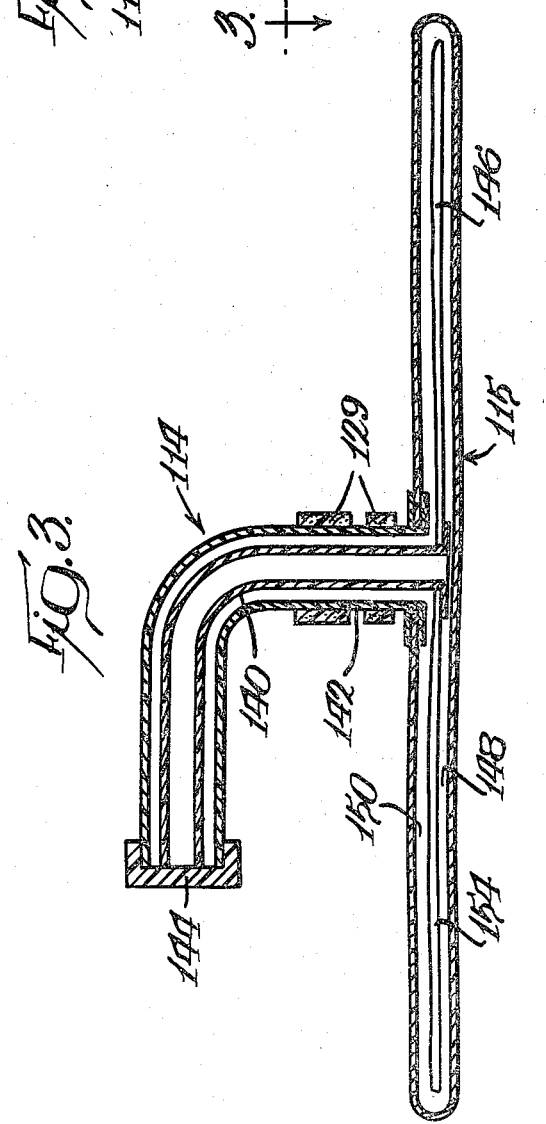

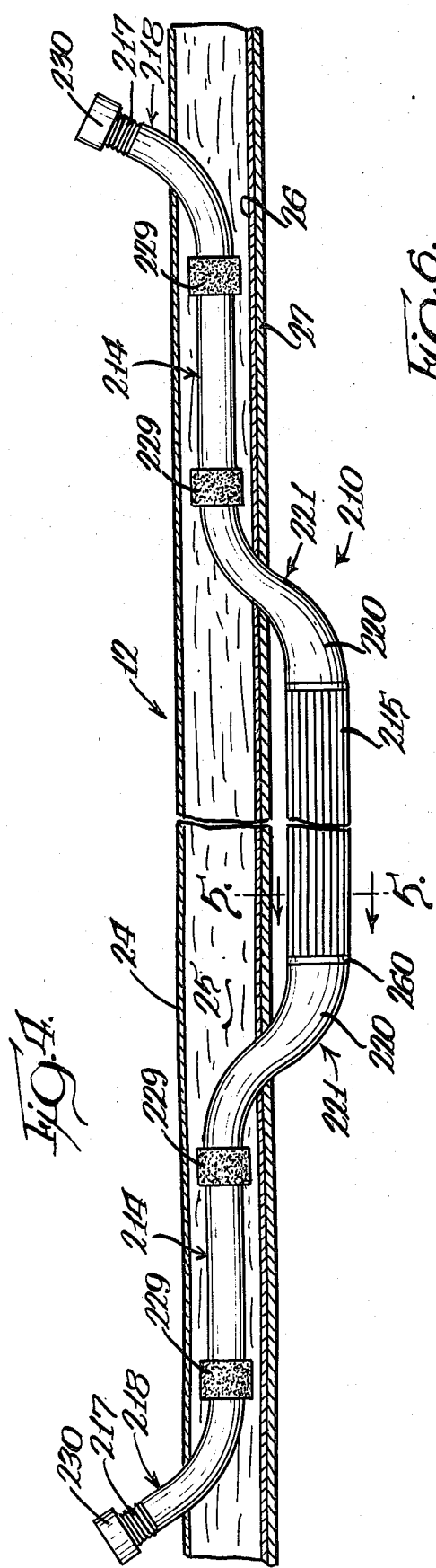
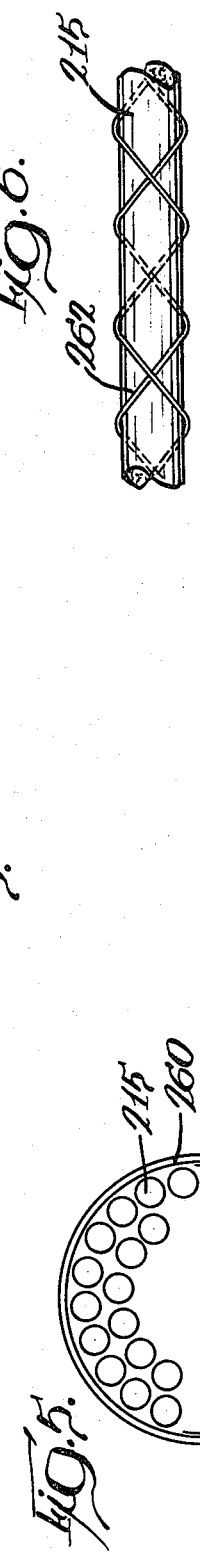
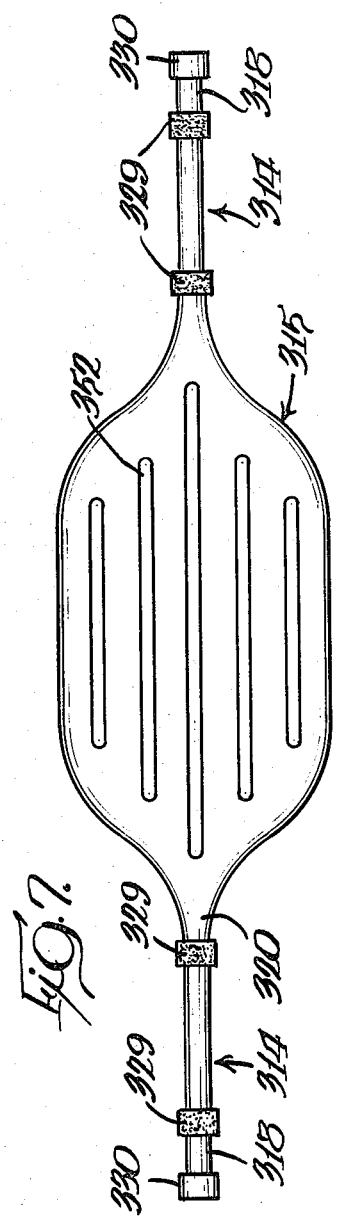

BODY CAVITY ACCESS DEVICE CONTAINING A HORMONE SOURCE

TECHNICAL FIELD

This invention relates to a structure and method for providing a hormone supply to a patient.

BACKGROUND OF THE INVENTION

Many diseases of the body are caused by a deficiency of certain endocrine gland hormones. These diseases include myxedema and diabetes mellitus. The endocrine glands are usually considered to include the thyroid, parathyroid, thymus, pituitary, pineal, adrenal, pancreas and the gonads. While a few hormones, e.g. thyroid hormone, may be taken orally, most hormones are digestable and must be injected.

There are several disadvantages with periodic injection of hormones. Since injections are painful and troublesome, and each injection represents a possibility for infection, injections are spaced at intervals as far apart as possible, resulting in peak and valley hormone concentrations. It has been found that more effective treatment results from a constant supply of hormones in accordance with the body's need. Constant control of the hormone level avoids the problems of peaks and valleys in medication.

To date, the best known detector to measure the body's demand for a particular hormone is the cell of the gland which produces that hormone. Such a cell not only measures the body's need, but also produces the necessary dosage of that hormone. The advantages of such cells are readily apparent in the case of diabetes and insulin demand.

Diabetes mellitus is a disease characterized by hypoglycemia, polyuria, and wasting. It is beneficial to maintain normal blood glucose levels in diabetics at all times, an objective difficult or impossible to achieve using insulin injection and diet. Two solutions have been suggested for achieving more physiologic patterns of insulin replacement. One approach uses a glucose sensor operably associated with an insulin injection system. A second approach implants live insulin producing tissue within the patient.

Transplantation of pancreatic tissue has met with limited success because of immune rejection reactions encountered due to the difficulty in obtaining a perfect tissue match. One solution to this problem is to encapsulate live hormone-producing cells within a membrane capsule as shown in U.S. Pat. No. 3,093,831 to Jordan. The membrane protects the cells from such reactions but allows the free passage of hormones and nutrients. The encapsulated hormone-producing cells can then either be injected or surgically implanted. For various reasons encapsulated cells once placed in the body only have a limited life span, usually measured in weeks.

Other methods have been to place insulin cells on one side of a membrane while blood flows on the other side of the membrane. However these devices are for extracorporeal use which has limits on blood flow access and these devices are not readily adaptable to implantation.

Since no means is presently known to keep implanted pancreatic cells alive and producing insulin at a useful rate indefinitely, periodic replacement is necessary. However, none of the previous implantable allows easy replacement of the cells from outside the body. What is needed is a method and structure for replacing live pancreatic islet cells or other hormone-producing cells from outside the body without having to surgically remove the entire implant.

This invention provides a system and method yielding an artificial endocrine gland with replaceable hormone-producing cells. This invention also provides a system and method yielding an artificial endocrine pancreas which utilizes live pancreatic islet cells as the hormone-producing cells.

SUMMARY OF THE INVENTION

The present invention discloses a method and structure for supplying a patient with hormones in which he may be deficient. A hormone source, e.g. hormone producing cells, a slow release hormone-containing composition, or the like are placed in a housing implanted in the patient and those cells may be replaced from outside the patient should the need arise. The housing also allows the placement of a sensor and the release of hormones into a patient from an external source while protecting the patient from possible infection.

The housing comprises an impermeable hollow stem passing through a body site such as the abdominal wall and a semipermeable membrane sack of relatively large surface area attached to the stem and positioned inside the patient, e.g., within the peritoneal cavity. The sack allows hormones, nutrients, oxygen and waste products, to flow in and out of the housing while preventing bacteria from entering the patient.

A sensor may be positioned in the sack for diagnostic or monitoring purposes to measure properties of the patient's body fluid. Such a sensor, a glucose level sensor, is disclosed in our pending application Ser. No. 218,710 filed Dec. 22, 1980 as a continuation-in-part of Ser. No. 107,965 filed Dec. 28, 1979. Because the fluid within the sack will have obtained equilibrium with the patient's body fluid, the sensor is capable of making the same measurements as if it had been located directly within the body cavity. Should the sensor fail for any reason, it can easily be removed and replaced without the threat of infection to the patient. Additionally, a catheter for releasing a hormone such as insulin may have its end located within the sack. Insulin would then be released into the sack and diffuse out through the walls of the sack and into the patient. This protects the patient from possible contamination caused by the bacteria which may accidentally become present within the insulin.

Alternatively, hormone producing cells may be removably placed in the sack. The cells take over the function of the corresponding natural gland, sense the amount of hormone needed, and produce the correct amount of the desired hormone. The hormone passes through the semipermeable membrane into the patient's body fluids while nutrients, oxygen and in some cases other hormones, pass from the body fluids through the semipermeable membrane to the hormone producing cells. Since an exchange of hormones may take place in both directions through the membrane, the body itself regulates the course of hormone production as with a natural gland.

The present invention is especially useful in the treatment of diabetes where effective control of insulin and glucose levels has proved difficult. Because the semipermeable membrane sack prevents the passage of immune response bodies, it not only allows the use of live cells taken from another human lacking a perfect tissue match, but also the use of live pancreatic cells taken from other animals.

Numerous other features of the present invention will become readily apparent from the following detailed description of the invention and embodiments, from the claims and from the accompanying drawings.

BRIEF DESCRIPTION OF THE DRAWINGS

In the accompanying drawings forming part of the disclosure:

FIG. 1 is a cross-sectional view of a sensor, catheter, and housing comprising a stem and sack shown implanted in a patient;

FIG. 2 is a cross-sectional, elevational view showing an alternative housing having a generally flat disc-like sack and coaxial inlet and outlet stem members;

FIG. 3 is a bottom view of the embodiment shown in FIG. 2 showing heat sealed ribs reinforcing the structure of the housing;

FIG. 4 is an embodiment similar to FIG. 1, but having two stems and a plurality of membrane tubes within the patient;

FIG. 5 is a cross-sectional view taken along plane 5—5 of FIG. 4 showing the positioning of the tubes;

FIG. 6 is an enlarged view of one of the tubes showing spacing filaments wound about the tube; and FIG. 7 is an embodiment similar to FIG. 4, but having a generally flat membrane tube with two stems.

DESCRIPTION OF THE PREFERRED EMBODIMENTS

While this invention is susceptible to embodiment of many different forms, there are shown in the drawings and will be described in detail, preferred embodiments of the invention. It should be understood that the present disclosure is to be considered as an exemplification of the principles of the invention and is not intended to limit the invention to the embodiments illustrated.

The precise shapes and sizes of the components described are not essential to the invention unless otherwise indicated. For ease of description, the device of this invention will be described in its normal operating position and such terms as up, down, inside, outside, etc. will be used with reference to this position. The choice of materials is dependent upon the particular application involved and other variables as those skilled in the art will appreciate. The materials have to be physiologically compatible with the patient.

Referring now to the drawings, FIG. 1 shows a housing 10 for placement in the patient. The housing 10 is constituted by an impermeable hollow stem 14 and a semipermeable membrane sack 15. The hollow stem has a distal end 17 defining an extracorporeal segment 18 and a proximal end 20 defining a subcutaneous segment 21. The sack 15 is adapted to receive a hormone source, e.g., live hormone-producing cells and has an access opening 22 which is coupled to the proximal end 20 of the hollow stem 14. The stem 14 defines an access passageway to the sack 15. A seal means such as plug 30 seals the distal end 17 of the stem 14. Although the sack 15 is shown to have a generally tubular shape, it is understood that the sack may have any suitable configuration including a generally hollow disk shape.

The housing 10 is surgically implanted in a patient through the abdominal wall. The abdominal wall 12 is shown here to have an epidermis 24, subcutaneous fat 25, fascia 26 and a peritoneal membrane 27. Peritoneal fluid surrounds the sack 15 of the implanted housing 10.

The distal end 17 of the hollow stem 14 has a flexible zone 28 comprising a plurality of circumferential grooves and extends beyond the body of the patient allowing access to the sack 15 through the hollow stem 14 from outside the body. Preferably, a portion of the subcutaneous segment 21 for placement in the subcutaneous fat 25 is surrounded by one or more porous cuffs 29 which promote ingrowth of tissue to help anchor the stem and help prevent infection. It is more preferred that at least two cuffs be used, and that there be some distance between cuffs to further increase the area for ingrowth of tissue and to decrease the possibility of infection. Implantation of such an access stem is discussed by Tenckhoff et al., "A Bacteriologically Safe Peritoneal Access Device," Trans. Amer. Soc. Artif. Int. Organs 14:181 (1968) which is incorporated by reference to the extent pertinent.

Also shown in FIG. 1 is a sensor 31 attached to a transmission line 32. The sensor 31 may be any type of sensor to determine any body function or condition, but preferably is an osmolality sensor for the determination of glucose levels as disclosed in our copending application Ser. No. 218,710 filed Dec. 22, 1980 and incorporated by reference. Such a sensor may be operably associated with a control device (not shown) which would regulate the release of medication such as a hormone into the membrane sack 15 through cannula 35.

The patient is protected should any bacteria or other foreign matter somehow enter the sack. Only the medication can pass through the small pores of the membrane sack 15. The membrane material of this sack is discussed in more detail below. In place of or together with the sensor and cannula, live hormone producing cells may be placed in the sack 15.

An alternative housing 110 having a disc-like sack 115 providing a large surface area for hormone transfer is shown in FIG. 2. The stem 114 comprises an inner stem member 140 within an outer stem member 142, surrounding part of the outer stem member 142 is at least one, preferably two, porous cuffs 129. The stem members are preferably coaxial and jointly closed by a single closure unit such as plug 144.

Located within the disc-shaped sack 115 is a separating wall plate 146 attached to the inner stem member 140. The separating wall plate 146 divides the interior space or chamber of the sack 115 into a first chamber section 148 and a second chamber section 150. As hormone producing cells are introduced under slight pressure through the interior stem member 140, they pass into the first chamber section 148 then about the periphery of the separating wall plate 146 and into the second chamber section 150. This ensures that hormone producing cells are evenly distributed throughout the sack 115 and a flow-through passage is created by the separating wall plate 146. This provides an even distribution over a large surface area and insures an efficient transfer of hormones and nutrients into and out of the housing 110.

To reinforce the sack 115, a plurality of sealing connections 152 may be made between the walls of the sack and the separating wall plate 146. (FIG. 3). The separating wall plate 146 may also be provided with ridges 154. The ridges 154 and sealing connections 152 add strength to the housing 110 and insure an open flow path across the surface of the disc-like sack 115. The connections 152 also maintain a set thickness to the chamber sections 148 and 150 to insure that cells located in the housing 110 are not far from the surface of the sack 115. Generally the chamber sections 148 and 150 have a thickness of about 0.5 millimeters to about 5 millimeters. The overall diameter of sack 115 is about 50 to about 150 millimeters.

In a further preferred embodiment shown in FIGS. 4-6, the housing 210 generally comprises two stems 214 in fluid communication with a bundle of tubes 215. Each stem has a distal end 217 defining an extracorporeal segment 218 and a proximal end 220 defining a subcutaneous segment 221. Seal means such as plugs 230 seal the distal ends 217. Preferably each tube 215 constituting the bundle has an inside diameter from about 200 microns to about 1,000 microns. The tubes are preferably are spaced from one another and connected by a flow-dividing unit 260 which places the tubes in a sealed fluid communication with the stems 214. The dividing unit 260 may be constructed using principles well-known in the dialysis art. Illustrative of such a method is disclosed in U.S. Pat. No. 3,708,071 to Crowley, incorporated herein by reference to the extent pertinent.

As many as a hundred tubes 215 may be used in a bundle according to this embodiment. Although the flow dividing unit 260 is shown with a generally circular cross-section in FIG. 5, this unit and hence the positioning of the tubes 215 may have any appropriate cross-section including generally rectangular or eliptical.

Preferably, some of the tubes, or more preferably all of the tubes, are provided with a spacer means such as a filament 262 wound helically about the tube as shown in FIG. 6. This maintains the space between tubes to aid the free flow of body fluids through and about the tubes. Such flow is desirable to ensure that there is a constant flow of nutrients, oxygen and hormones into and out of the housing 210.

As with the other embodiments, each of the access stems 214 of the embodiment shown in FIG. 4 preferably is provided with two porous cuffs 229 which are spaced to allow the in-growth of tissue to help prevent infection and to hold the housing 210 in place.

Another embodiment similar to that of FIG. 4 is shown in FIG. 7. A single tube 315 with a generally broad, flattened construction is provided. The tube 315 is in fluid communication with the proximal ends 320 of two access stems 314 which have plugs 330 removably mounted on their distal ends 318 and provides a hormone transfer. This embodiment is preferably provided with a plurality of porous cuffs 329 on each of the access stems. The broad, flattened tube 315 may be reinforced with ribs 352 which may be formed by heat sealing the two opposite walls of the tube along linear portions. The tube 315 preferably has a width across its broad section of about 75 milimeters and a thickness of about 1-5 millimeters.

The advantage of the embodiments shown in FIGS. 4-7 is that there are two access passageways which allow the insertion and removal of hormone producing cells into their respective tubes. It is easier to place and remove cells by applying a small pressure at one stem, while introducing a small vacuum at the other. This effectively sweeps out the old cells which are no longer functioning properly and allows easier replacement with new viable cells.

In the embodiments illustrated, either a combination of sensor and a hormone releasing cannula may be located within the housings or hormone producing cells may be placed in the housing. These hormone producing cells can be taken from an organ such as the pancreas that produces the desired hormone. Alternatively genetically altered bacteria may be used. Hormone producing cells may be prepared by growing in culture to obtain a relatively pure source of cells. One such method is disclosed by Chick et al., "Pancreatic Beta Cell Culture: Preparation of Purified Monolayers" Endo 96:637 (1975) incorporated by reference to the extent pertinent. Alternatively the cells may be removed from a fresh organ. The cells are then suspended in solution and placed into the housing.

Instead of a suspension of cells, microencapsulated live hormone producing cells surrounded by semipermeable membrane may be used. Each microcapsule has a diameter of approximately 100-300 microns, allowing a plurality of such microcapsules to be placed in the housing. Because of their small size, the microcapsules have a high surface area to volume ratio allowing ready access of nutrients and oxygen to the cells and dispersal of the hormone produced and waste products from the cells. A method of producing such microencapsulated cells is disclosed, by Lim et al., "Microencapsulated Islets As Bio-Artificial Endocrine Pancreas", Science 210:908 (1980) and is incorporated herein by reference to the extent pertinent.

Many materials can be used to form the membrane sacks and tubes. Examples of suitable materials are cellulose, cellulose hydrate, cellulose acetate, various cellulose esters, polycarbonate membranes of the type disclosed in U.S. Pat. Nos. 4,075,108 and 4,160,791 to Higley et al., poly(vinyl alcohol) membranes of the type described in U.S. Pat. No. 4,073,733 to Yamauchi et al., microporous poly(ethylene) and poly(propylene) films, cross linked alginate (a non-toxic polysaccharide), poly(2-hydroxyethylmethacrylate) and poly(2,3-dihydroxypropylmethacrylate) films, and the like. The preparation of such membranes is disclosed in U.S. Pat. No. 4,075,092 to White et al., Klomp et al., "Hydrogels for Encapsulation of Pancreatic Islet Cells", Trans. Amer. Soc. Artif. Int. Organs 25:74 (1979), Lim et al., "Microencapsulated Islets as Bioartificial Endrocine Pancreas" Science 210:908 (1980), and Lee et al., *Handbook of Biomedical Plastics,* Pasadena Technology Press, Pasadena, California (1971). All of the foregoing references are incorporated herein by reference to the extent pertinent. PAN (a polyacrylonitrile membrane available from Rhone-Ponlanc) may also be used. Polycarbonate membranes are particularly advantageous because they are heat sealable and are entirely nonbiodegradable. This allows easy construction and a long life span. One such polycarbonate membrane is BARD PCM available from C. R. Bard, Inc.

A membrane-like filter can be used in place of the membrane. Such a filter, disclosed in U.S. Pat. No. 4,141,838 to Schilling and incorporated by reference to the extent pertinent, allows the passage of nutrients, oxygen and hormones and prevents the passage of bacteria and large proteins.

The membrane material chosen may then be treated with heparin to minimize deposits of fibrin in a manner known to those skilled in the art. Illustrative such treatments is the method disclosed in U.S. Pat. No. 3,441,142 to Oja, incorporated by reference to the extent pertinent.

The choice of the material for the sack or tube depends on several factors. There should be permeability for desirable molecules such as nutrients, oxygen and hormones, and impermeability to undesirable elements such as bacteria and possibly immune response elements. To prevent the passage of bacteria the membrane should have an effective pore size less than about 0.5 microns. It is preferred that the membrane be impermeable to such immune response bodies as immunoglobulins which have molecular weights greater than 50,000 to 150,000 daltons. Such a membrane would then have a pore size of approximately 40-50 Angstroms. This allows the passage of nutrients which generally have molecular weights less than 200, as well as the passage of hormones such as insulin which has a molecular weight of approximately 6400, and prevents the passage of bacteria which may be accidentally introduced within the device. In general, it is desirable that the pores be as large as possible, allowing a free flow of nutrients and hormones while still protecting the patient.

To facilitate the transfer of nutrients and hormones, it is desirable that the membrane have a thickness of 200 microns or less. However, membranes of thickness as low as 20 microns can be used as long as they exhibit suitable permeability and adequate strength. The exterior surface of the membrane sack or tube can be reinforced with an open mesh made of polyethylene or the like to add resiliency, strength, and resistance to breakage. The sack or tube membrane preferably is treated with heparin to decrease formation of fibrin on the outside surface in contact with the peritoneal fluid.

The foregoing specification is intended as illustrative and is not to be taken as limiting. Still other variations within the spirit and scope of this invention are possible and will readily present themselves to those skilled in the art.

What is claimed is:

1. An implantable device for providing safe access to a patient's body cavity comprising:
    (a) a housing constituted by a sack and a hollow stem; the sack having at least one access opening and being constructed of a semipermeable membrane compatible with body tissue and permeable to peritoneal fluid but substantially impermeable to bacteria; the hollow stem having a distal end defining an extracorporeal segment and a proximal end defining a subcutaneous segment, the stem being compatible with body tissue and impermeable to body fluids; the sack access opening being sealingly coupled with the proximal end of the stem and together with the stem defining an access passageway to the sack, the housing being adapted to be implanted in the patient with the extracorporeal segment extending outside the body of the patient;
    (b) a plug to seal the distal end of the stem; and
    (c) a sensor to measure properties of body fluid located within the sack, the sensor having a transmission line extending outside the housing, and including a cannula extending into the housing to deliver medication into the sack.

2. The implantable device of claim 1 including at least one porous cuff surrounding a portion of the subcutaneous segment of the hollow stem.

3. The implantable device of claim 1 wherein the extracorporeal segment includes a flexible zone comprising a plurality of circumferential grooves.

4. The implantable device of claim 1 wherein the sack has a membrane with an effective pore size less than about 0.5 microns.

5. The implantable device of claim 4, wherein the pore size is sufficient to substantially prevent the passage of molecules having a molecular weight greater than about 50,000 daltons.

6. The implantable device of claim 1 including a hormone source situated within the sack.

7. The implantable device of claim 1 including live hormone producing cells removably placed within the housing.

8. The implantable device of claim 7 wherein the hormone producing cells are pancreatic islet cells.

9. The implantable device of claim 1 wherein the sack has a generally tubular shape having two ends, one end closed and the other end defining the access opening.

10. The implantable device of claim 1 including a second stem having a distal end defining an extracorporeal segment and a proximal end defining a subcutaneous segment, the second stem being compatible with body tissue and impermeable to body fluids, and wherein the sack has a generally tubular shape having two access openings sealingly coupled with the proximal end of each stem to form a hose with each stem defining an access passageway to the sack.

11. An implantable device for providing safe access to a patient's body cavity comprising:
    (a) a housing constituted by a sack and a hollow stem; the sack having a generally disc-like shape defining a chamber in fluid communication with the stem, at least one access opening, and being constructed of a semipermeable membrane compatible with body tissue and permeable to peritoneal fluid but substantially impermeable to bacteria; the hollow stem having a distal end defining an extracorporeal segment and a proximal end defining a subcutaneous segment, the stem being compatible with body tissue and impermeable to body fluids; the sack access opening being sealingly coupled with the proximal end of the stem and togehter with the stem defining an access passageway to the sack, the housing being adapted to be implanted in the patient with the extracorporeal segment extending outside the body of the patient;
    (b) a plug to seal the distal end of the stem; and
    (c) a separating wall plate dividing the chamber into a first chamber section and a second chamber section, the chamber sections being in fluid communication about the periphery of the plate and wherein the stem is constituted by an extermal stem member attached to the sack and in fluid communication with the second chamber section and an internal stem member located within the external stem member and in fluid communication with the first chamber section.

12. The implantable device of claim 11 wherein the chamber sections have a height between the plate and the sack of about 0.5 millimeters to about 5 millimeters.

13. An implantable device for supplying hormones to a patient comprising:
    (a) a housing constituted by a plurality of tubes and two hollow stems and including a flow dividing unit to place the tubes in sealed fluid communication with the stems; each of the tubes having two open ends and being constructed of a membrane compatible with body tissue and permeable to body fluids but substantially impermeable to bacteria; each stem having a distal end defining an extracorporeal segment and a proximal end defining a subcutaneous segment, each stem being compatible with body tissue and impermeable to body fluids; each end of each tube sealingly coupled with the proximal end of each stem such that each stem defines an access passageway to the tubes;
(b) live hormone producing cells within the housing; and
(c) plugs to seal the distal end of each stem.

14. The implantable device of claim 13 including at least one porous cuff surrounding a portion of the subcutaneous segment of each hollow stem.

15. The implantable device of claim 13 wherein the hormone producing cells are pancreatic islet cells.

16. The implantable device of claim 13 including spacer means on at least some of the tubes for maintaining a space between tubes.

17. The implantable device of claim 13 wherein the tubes have an inside diameter of about 200 microns to about 1000 microns.

18. The implantable device of claim 13 wherein each tube has a broad flattened construction.

19. The implantable device of claim 13 wherein the tubes have a membrane with an effective pore size of less than about 0.5 microns.

20. The implantable device of claim 13 wherein the pore size is sufficient to substantially prevent the passage of molecules having a molecular weight greater than about 50,000 daltons.

* * * * *